United States Patent [19]

van der Veek

[11] 4,041,145
[45] Aug. 9, 1977

[54] SELENYL AND TELLURYL DERIVATIVES OF STEROIDS

[75] Inventor: Augustinus Petrus Maria van der Veek, Voorschoten, Netherlands

[73] Assignee: Philips-Duphar B.V., Amsterdam, Netherlands

[21] Appl. No.: 636,099

[22] Filed: Nov. 28, 1975

[30] Foreign Application Priority Data

Nov. 28, 1974 Netherlands .......................... 7415526

[51] Int. Cl. .......................... A61k 43/00; C07j 9/00
[52] U.S. Cl. ...................................... 424/1; 260/397.2
[58] Field of Search ........................ 260/397.2; 424/1

[56] References Cited

U.S. PATENT DOCUMENTS 3,697,297 10/1972 Churchill ............................ 106/131
3,888,892 6/1975 Leder ................................ 260/397.2

*Primary Examiner*—Elbert L. Roberts

*Attorney, Agent, or Firm*—Hammond & Littell

[57] ABSTRACT

Selenyl- and telluryl derivatives of steroids are prepared having in general the formula of 19-methylselenyl or 19-methyltelluryl derivatives respectively of cholesterol and related 3-oxy 5-Δ-steroids, such as sitosterol and campesterol.

More specifically these substances are prepared with radioactively labelled Se and Te atoms by first preparing compounds of the type of alkyl lithium selenides and tellurides respectively and related compounds and these are reacted with steroid compounds of the type stated having a smoothly transferable substituent in the 19 position.

These labelled compounds are suitable for preparing diagnostic compositions for examination into internal organs such as the adrenal glands, applying scintigraph detection methods. They also can be applied for radio-immunologic determinations and other diagnostic determination methods.

20 Claims, 5 Drawing Figures (1)
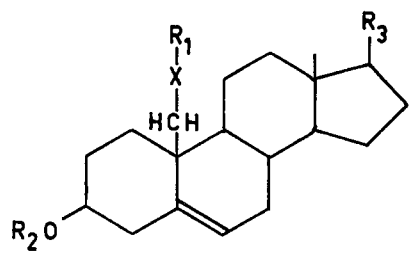
(2)
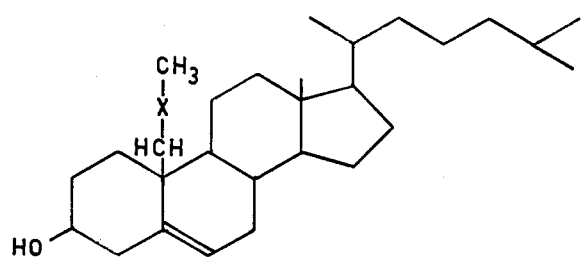
(3) 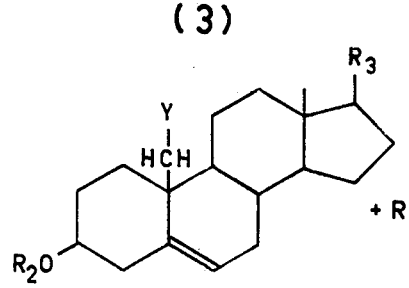 (4) 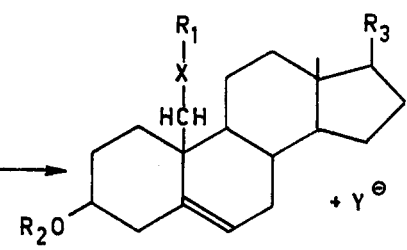

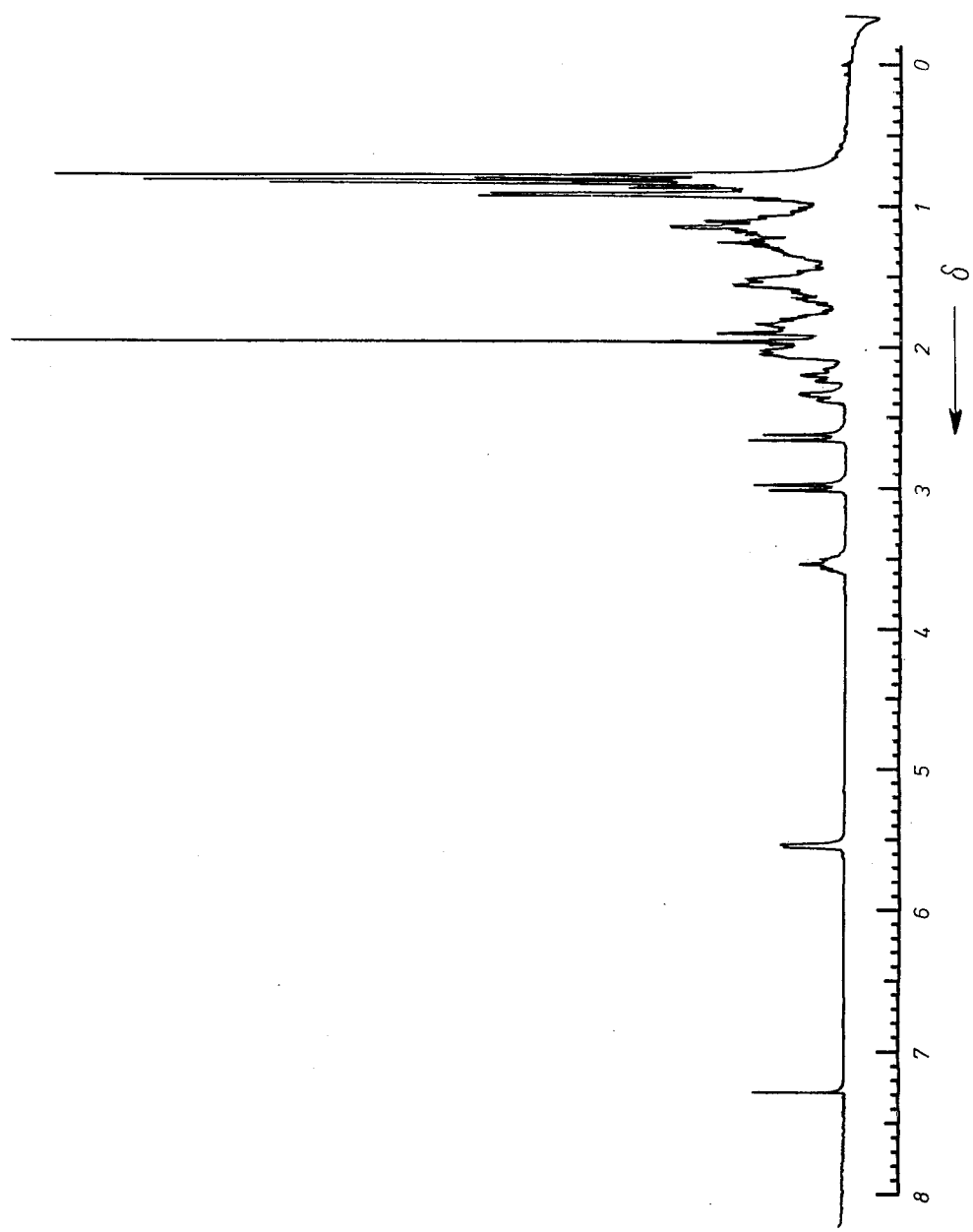

SELENYL AND TELLURYL DERIVATIVES OF STEROIDS

BACKGROUND OF THE INVENTION

The invention relates to novel selenyl- and telluryl derivatives of steroids and to methods for the preparation of these compounds, as well as to the application of such compounds, labelled with radioactive selenium and tellurium isotopes, in diagnostic compositions in particular to be used with a method for diagnostic investigation into abnormalities of internal organs, viz. of the adrenal gland and with a radio-immunologic determination of the steroid-level in the blood or the urine.

For the diagnostic investigation into abnormalities of internal organs, viz. the adrenal gland, according to the so-called "scintigraphic" methods, use has been made already of 19-iodocholesterol labelled with iodine-isotopes $^{125}I$ and $^{131}I$ that after intravenous administration is found to accumulate itself sufficiently in the adrenal gland so as to be able to make a scintigram of it (See the publications by W. H. Beierwaltes, R. E. Counsel et al in J. Nucl. Med. 12, No. 4 (1971), 176, J. Am. Med. Assoc. 216, No. 2 (1971), 275, J. Clin. Endocrin. and Metab. 33 (1971), 713 and J. Nucl. Med. 14, No. 11 (1973),777).

A drawback of working with this radio-actively labelled 19-iodocholesterol is for instance the high irradiation load, viz. the thyroid gland being overloaded (see J. Nucl. Med. 14, No. 9 (1973), 713) and the poor stability of the compound, both in vivo and in vitro (see J. Nucl. Med. 15, No. 1 (1974), 38).

SUMMARY OF THE INVENTION

Now it was found that these drawbacks of 19-iodocholesterol labelled with $^{125}I$ and $^{131}I$ for the application mentioned can be entirely or partly removed by using instead of 19-iodocholesterol a 19-selenyl- or 19-telluryl derivative of cholesterol or a compound related to it, which has been labelled with a selenium or a tellurium isotope, respectively. Preferably, for this purpose the isotopes $^{75}Se$ and $^{123m}Te$, respectively, are used.

As advantages of the use of these labelled 19-selenyl steroids over labelled 19-iodocholesterol can be stated: the greater stability in vivo and in vitro, the fact that little or no activity goes to the thyroid gland and the diminished irradiation load for the patient, also because the dose to be administered can be smaller. In this respect it is pointed out that the isotopes $^{75}Se$ and $^{123m}Te$ are γ-irradiators, whereas $^{131}I$ besides a γ-irradiator is also a β-irradiator and $^{125}I$ is a γ-irradiator with a low γ-energy, which is highly absorbed in the body and in compositions.

Furthermore, it has been found that the mentioned 19-selenyl and 19-telluryl derivatives of steroids can also be used for other diagnostic determination methods, e.g. for the in vitro determination of hormones in blood and urine with the aid of radio-immunological techniques. Here again, $^{75}Se$- and $^{123m}Te$-isotopes offer the advantage that they are γ-irradiators and consequently are more easily to be determined than e.g. the low-energetic β-irradiators $^{14}C$ and $^{3}H$. In particular, $^{75}Se$ offers the advantage of the greater stability over $^{125}I$ and $^{131}I$, respectively. On the other hand, $^{123m}Te$ offers the advantage of being a more specific γ-irradiator, which might make the telluryl compounds preferable for scanning of the adrenal gland.

BRIEF DESCRIPTION OF THE DRAWING

The formula sheet shows the general formula (1), the more specified formula (2) and the general reaction by which a substituted steroid (3) is converted into the corresponding compound (4), which is similar to compound (1).

FIG. 1, further, shows the NMR spectrum of 19-methyl selenyl sitosterol.

DETAILED DESCRIPTION OF THE INVENTION

Thus the invention relates to novel selenyl- and telluryl derivatives of steroids, having general formula (1)

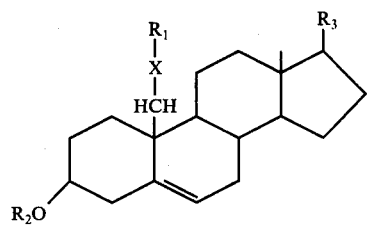

in which X represents a selenium or tellurium atom, $R_1$ is a hydrocarbon radical, $R_2$ is a hydrogen atom, an alkanoyl group or an organic group that in a simple way can be linked to, or removed from the oxygen atom, and $R_3$ is a 1,5-dimethyl hexyl group, which, if desired may carry a methyl- or ethylsubstituent at the 4-position.

In the said general formula (1) shown in the formula sheet $R_1$ preferably is an alkyl group, e.g. a methyl- or n-butylgroup, but $R_1$ may, for instance, also be a cycloalkyl-, aryl- or aralkyl group, or an unsaturated group such as an alkenylgroup. Examples of organic groups $R_2$, which in a simple way can be linked to the oxygen atom or removed from it, respectively, are: acetals and labile ether- or hemiacetal groups.

A preferred compound according to the invention is 19-methyl selenyl- or 19-methyl telluryl cholesterol, respectively, having formula (2) of the formula sheet, in which X represents a selenium or tellurium atom.

Other compounds according to the invention are, for instance, the 19-methyl selenyl-cholesterol linoleic acid ester, 19-methyl selenylcholesterol tetrahydropyranyl ether, 19-methyl selenyl-sitosterol, 19-methyl selenyl-campesterol and the corresponding 19-methyl telluryl compounds. The linoleic acid ester of 19-methyl selenyl- or 19-methyl telluryl-cholesterol may be of advantage over the parent hydroxy compound in that it is more rapidly taken up by the blood. Sitosterol derivatives might be preferable over the corresponding cholesterol derivatives because they do not raise the cholesterol level.

The selenyl- and telluryl compounds according to the invention can be prepared, starting from their corresponding steroids, by firstly preparing a derivative, having general formula (3) of the formula sheet in which on site 19 a substituent Y is present that can easily be transferred. This substituted steroid subsequenty is caused to react with a solution of an alkyl-, alkenyl-, cycloalkyl-, aryl- or aralkyl selenide or telluride, respectively, to form the desired 19-alkyl-, 19-alkenyl-, 19-cycloalkyl-, 19-aryl- or 19-aralkyl selenyl-, or telluryl steroid, respectively. This last mentioned nucleophilic substitution reaction can be shown by the reaction scheme of the formula sheet, in which X, $R_1$, $R_2$ and $R_3$ have the meanings as defined in respect of formula 1) of the formula sheet and Y represents a group that can easily be transferred.

The easily transferable substituent Y can, for instance, be a halogen atom, in particular a bromine atom, or a p-toluene-sulphonate radical. The derivatives of steroids that on site 19 contain such an easily transferable substituent, can be obtained in ways known in the art, for instance, by conversion of the corresponding 19-hydroxysteroid.

Methods for the preparation of 19-hydroxysteroids are, for instance, known from J. Am. Chem. Soc. 86 (1964), 1528 and Helv. Chem. Acta 46 (1963), 1361.

Solutions of alkyl-, alkenyl-, cycloalkyl, aryl- or aralkyl selenides or -tellurides, respectively, which can be used in the above method, can be, for instance, solutions of the corresponding alkyl-, alkenyl-, cycloalkyl-, aryl- or aralkyl lithium selenides or tellurides, respectively, in a polar aprotic solvent, such as e.g. dimethoxyethane, triethylene-glycol dimethyl ether or tetrahydrofuran, or in a mixture of such solvents. In such solutions, which themselves can be prepared by a reaction of lithium alkyl, alkenyl, cycloalkyl, aryl or aralkyl compounds with metallic selenium or tellurium, a dissociation occurs, as shown in the reaction scheme:

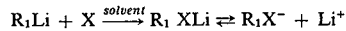

$$R_1Li + X \xrightarrow{solvent} R_1XLi \rightleftharpoons R_1X^- + Li^+$$

A preparation method for a solution of lithium methyl selenide, which can be used in preparing compounds according to the invention, is, for instance, the preparation of selenomethionine known from patent application Ser. No. 41,444 filed May, 28, 1970, now abandoned.

It may be desirable or necessary for the preparation of 19-selenyl- and 19-telluryl derivatives, having formula 1) of the formula sheet, in which $R_2$ is a hydrogen atom, to protect the hydroxy group present at site 3, e.g. by acetylating or benzoylating it. This protecting group may be removed again, if desired, during or after the reaction with the alkyl-, alkenyl, cycloalkyl-, aryl- or aralkylselenide, or -telluride, respectively. If compounds, having formula (1) of the formula sheet are represented, in which $R_2$ is an organic group that in a simple way can be linked to, or removed from the oxygen atom respectively, this group can be introduced already before the reaction with the alkyl-, alkenyl-, cycloalkyl-, aryl- or aralkylselenide, or -telluride, respectively, is carried out, but this introduction can also be carried out after that.

It stands to reason, that for the preparation according to the invention of the 19-selenyl or 19-telluryl-steroids, respectively, labelled with radioactive selenium- or tellurium-isotopes, respectively, the same methods of preparation can be used as described above.

A further aspect of the invention relates to diagnostic compositions, containing a selenyl- or telluryl derivative of a steroid that is labelled with a selenium- or a tellurium-isotope, has the general formula (1) of the formula sheet and is brought into an administration form suitable for diagnostic purposes. This bringing into an administration form suitable for diagnostic purposes may, for instance, be carried out by mixing the selenyl- or telluryl derivatives of a steroid with a liquid or solid carrier that can be tolerated by the human body.

These diagnostic compositions, containing an amount of radioactively labelled selenyl- or telluryl derivative of a steroid, having general formula (1) of the formula sheet, can be used for the diagnostic investigation into abnormalities of internal organs, viz. the adrenal glands, according to so-called scintigraphic methods. In a further aspect the invention consequently relates to a method for the diagnostic investigation into abnormalities of internal human and animal organs, in which a radio-active indicator substance is administered and by means of comparitive irradiation measurements the distribution of this indicator substance over certain organs is determined, which method is characterized in that the indicator substance used is a selenyl- or telluryl derivative of a steroid that is labelled with a radio-active selenium- or tellurium-isotope, respectively, and that has the general formula (1) of the formula sheet. Preferably, for this method use is made of 19-methyl selenyl cholesterol- $^{75}$Se, although, as said before, also other compounds of this invention may be used with advantage.

The diagnostic compositions according to the invention can, as has been said, also be used for other diagnostic determination methods in vitro, such as for radio-immunologic determinations in blood and urine.

The invention is further elucidated with reference to the following.

COMPARATIVE EXAMPLES

EXAMPLE I

Preparation of 19-methylselenyl cholesterol from 19-bromocholesterylacetate (a) 19-bromocholesterylacetate 2.15 gms. of triphenylphosphine and 2.85 gms. of tetrabromomethane were added to a solution of 1.65 gms. of 19-hydroxy cholesterylacetate [prepared according to the method of J. Am. Chem. Soc. 86(1964), 1528] in 70 mls. of dry ether and 10 mls. of dry m-xylene. A white precipitate of triphenylphosphine oxide was formed. Then the mixture was refluxed for 20 hours, the progress of the reaction being examined with the aid of thin-layer chromatography (toluene/ethyl acetate 3:1; silica gel H). After completion of the reaction 100 mls. of n-hexane and 0.5 mls. of methanol were added and approx. 15 minutes later the mixture was filtered and the filtrate evaporated. The residue was taken up in 10 mls. of ether and thereafter 15 mls. of n-hexane were added. Then this hexane/ether mixture was brought on to a column filled with 40 gms. of deactivated $Al_2O_3$ and subsequently was eluated with an ether/n-hexane mixture (2:3). The composition of the column fractions was examined with the aid of thin-layer chromatography. The fractions, in which 19-bromocholesterylacetate was present, ($R_f$= 0.7) were collected and evaporated at a film evaporator. Upon crystallization of the residue from ether/methanol, 1.45 gms. of the product were obtained, having a melting point of 91°–92° C. The structure was confirmed by means of NMR- and mass-spectrometry.

(b) 19-methylselenyl cholesterol 3 mls. of tetrahydrofuran, freshly distilled from LiAlH$_4$, were added to 127 mgs. of powdered metallic selenium under oxygen-free conditions. While the mixture was stirred, methyl lithium in tetrahydro furan was added dropwise, at temperatures of from 0° to −10° C, until the solution that initially was dark red, remained colourless for 5 minutes. To the solution of methyllithiumselenide in tetrahydro furan thus prepared at first 0.5 mls. of methanol and then a solution of 553 mgs. of 19-bromocholesterylacetate in 8 mls. of tetrahydro furan was added, whereupon this mixture, while oxygen was excluded as completely as possible, was kept at ambient temperature for 7 days.

After the addition 2 mls. of 2M $(NH_4)_2SO_4$-solution the reaction mixture was evaporated to a volume of approx. 2 mls., whereupon 10 mls. of benzene were added. The benzene layer was separated and then the aqueous layer was extracted for another two times with 5 mls. of benzene, whereupon the benzene-extracts were collected, dried over anhydrous $Na_2SO_4$ and evaporated to approx. 2 mls. This residue was mixed with 20 mls. of n-hexane and the mixture brought on to a column, filled with 20 gms. of $Al_2O_3$. The column was successively eluated with n-hexane/water mixtures 95:5, 90:10, 85:15, 80:20, 70:30 and 50:50. With the n-hexane/ether mixture 70:30 the 19-methylselenyl cholesterol was obtained from the column.

The fractions is question were evaporated and the residue crystallized from water/methanol. 253 mgs. of product were obtained, having a melting point of 135°–136° C. According to thin-layer chromatography (toluene/ethylacetate 7:3, silica gel H) this product was pure. The structure was confirmed by means of NMR- and mass-spectrometry.

EXAMPLE II

Preparation of 19-methylselenyl cholesterol from 19-(p-toluenesulphonyl)- cholesteryl acetate Starting from 134 mgs. of powdered metallic selenium, a solution of methylselenide in tetrahydro furan was prepared in the way as described in example I. To this were added 0.5 mls. of methanol and then a solution of 632 mgs. of 19-(p-toluene sulphonyl) cholesterylacetate [prepared according to J. Am. Chem. Soc. 86 (1964), 1533] in 6 mls. of tetrahydro furan. After this mixture had been kept at ambient temperature for three days, 2 mls. of 2 M $(NH_4)_2SO_4$-solution were added, the mixture was evaporated to a volume of approx. 2 mls., extracted with benzene and worked up further according to the method as described in example I(b).

204 mgs. of product were obtained, having a melting point of 135°–136° C, which was pure according to thin-layer chromatography. NMR- and mass-spectrometry confirmed the structure.

EXAMPLE III

Preparation of 19-methyl telluryl cholesteryl acetate from 19-(p-toluene sulphonyl)-cholesteryl acetate Starting from 98 mgs. of powdered metallic tellurium, in the way as described in example I, a solution of methyl telluride in tetrahydro furan was prepared. To this 6.8 mls. of a 0.16 molar solution of acetic acid in tetrahydro furan were added and then a solution of 366 mgs. of 19-(p-toluene sulphonyl) cholesteryl acetate in 5 mls. of tetrahydro furan. After this mixture had been kept at ambient temperature for 5 days it was evaporated to dryness. The residue thus obtained was taken up in 1 ml. of 10% acetic acid and 15 mls. of benzene; this two-phase system was filtered over anhydrous sodium sulphate that then was rinsed again with approximately 10 mls. of benzene. The total filtrate was evaporated to dryness, whereupon the residue was taken up in a mixture of 1 ml. of benzene and 10 mls. of n-hexane and worked up according to the method as described in example I(b).

100 mgs. of impure product were obtained in which according to NMR- and mass-spectrometrical examination the 19-methyl telluryl cholesterol acetate was present.

EXAMPLE IV

Preparation of 19-n-butyl selenyl cholesterol from 19-bromocholesteryl acetate

Under oxygen-free conditions 3 mls. of tetrahydro furan, freshly destilled from $LiAlH_4$, were added to 109 mgs. of powdered metallic selenium. While the mixture was stirred, hereafter, at temperatures of $-15°$ to $-20°$ C, a slight excess of n-butyl lithium in n-hexane was added dropwise. To the solution of n-butyl selenide in tetrahydro furan/hexane thus prepared, to first 0.3 mls. of methanol and then a solution of 515 mgs. of 19-bromocholesteryl acetate in 7 mls. of tetrahydro furan were added. After this mixture had been kept at ambient temperature for one day, it was heated for another 5 hours at 60° C. Then 1 ml. of 1.5 M $(NH_4)_2SO_4$ solution was added and 10 mls. of benzene. The two-phase system thus obtained was filtered over anhydrous $Na_2SO_4$ (thereafter it was rinsed with approximately 10 mls. of benzene). The filtrate was evaporated to dryness, whereupon the residue was taken up in a mixture of 1 ml. of benzene and 10 mls. of hexane and worked up according to the method as described in example I(b).

150 mgs. of impure product were obtained, which did neither become purer when column chromatography was repeatedly applied. Crystallization from hexane yielded 30 mgs. of product that, according to NMR- and mass-spectrometry, appeared to be substantially pure 19-butyl selenyl cholesterol. Evaporating to dryness of the mother liquor thus produced, followed by crystallization from 90% methanol, yielded 65 mgs. of a product that, according to NMR-spectroscopy consisted for approximately 90% of the 19-n-butyl selenyl cholesterol.

EXAMPLE V

Preparation of 19-methyl selenyl-cholesterol linolate from 19-methyl selenyl cholesterol To 140 mgs. of 19-methyl selenyl cholesterol, dissolved in 5 mls. of dry ether, were successively added 150 mgs. of fresh distilled linoleic acid chloride and 150 mgs. of triethyl amine dried on KOH. Then the mixture was refluxed for 3 hours, the precipitate produced was filtered off and the filtrate evaporated to dryness. The residue was mixed with 3 mls. of n-pentane and the mixture brought on to a column, filled with 10 grs. of $Al_2O_3$.

The column was eluated with n-pentane/benzene 9:1. The column fractions were examined on presence of ester with the aid of thinlayer chromatography and the pertinent fractions evaporated and yielded 20 mgs. of product. According to the thin-layer chromatography (toluene/ethyl acetate 3:1, silica gel on plastic HF; Merck) $R_f = 0,71$, this product was pure. The structure was confirmed by means of NMR- and mass-spectrometry.

EXAMPLE VI

Preparation of 19-methyl selenyl cholesterol-$^{75}$Se and of 19-methyl selenyl cholesteryl linolate-[75]Se (a) 19-methyl selenyl cholesterol-[75]Se (spec. act. 10mCi/m Mol)

Starting from 80 mgs. of powdered metallic selenium, having an activity of 10 mCi[75] Se, a solution of methyl selenide-75 Se in tetrahydro furan was prepared analogously to the method as described in example I(b). To this solution was added 1 ml. of methanol and then 400 mgs. of 19-bromocholesteryl acetate in 4 mls. of tetrahydro furan. After this mixture had been kept at ambient temperature for one day, it was heated for another day at 60° C. After addition of 100 mgs. of $NH_4Cl$ the mixture was evaporated to dryness. The residue was mixed with 7 mls. of benzene and transferred to a 50 cc flask. The equipment was rinsed again with 7 mls. of benzene and the collected benzene fractions were diluted with 40 mls. of n-hexane. Then they were worked up according to the method as described in example I(b).

1.5 m Ci of 19-methyl selenyl cholesterol-75 Se were obtained, which according to thin-layer chromatography and autoradiography was chemically and radiochemically pure.

(b) 19-methyl selenyl cholesteryl linolate-75 Se

Starting from 200 μ Ci of the above 19-methyl selenyl cholesterol-75 Se, dissolved in 5 mls. of dry ether, 19-methyl selenyl cholesteryl linolate-75 Se was prepared according to the method as described in example V. 50 μ Ci of product was obtained, which according to thin-layer chromatography followed by autoradiography, appeared to be approximately 90% pure 19-methyl selenyl cholesteryl linolate-75 Se.

EXAMPLE VII

Preparation of 19-methyl selenyl sitosterol (= 19-methyl selenyl 3 β-ol-stigmast-5-ene)

In an oxygen-free nitrogen atmosphere 1 ml. of tetrahydro furan, freshly distilled from $LiAlH_4$, was addd to 80 mgs. of powdered metallic selenium. While the mixture was stirred, hereinafter, at a temperature of −8° C, methyl lithium in tetrahydro furan was added dropwise until the solution which was initially dark red, remained colourless for 5 minutes. To the solution of methyl selenide thus prepared, at first was added 1 ml. of 0.078 M sulphuric acid in triethylene glycol dimethyl ether (triglyme), freshly distilled from $CaH_2$, and then a solution of 429 mgs. of 19-bromositosteryl acetate in 5 mls. of triethylene glycol dimethyl ether. After this mixture had been kept at ambient temperature for 2 hours, 1 ml. of 0.5 M sodium methoxide in methanol and 2 drops of water were added. This mixture was kept at ambient temperature for 1.5 hours. After addition of 1 ml. of 2 M $(NH_4)_2 SO_4$ in water the volatile components were removed from the reaction mixture. To the residue there were added 25 mls. of water, after which a precipitate was formed. After filtration, the precipitate was dried. In order to remove traces of water, the product was taken up in 50 mls. of diethylether and this ether-solution was evaporated again. The crude product was mixed with 3 mls. of hexane and the mixture was brought on to a column filled with 15 gs. of $Al_2O_3$. The column was successively eluated with n-hexane /ether mixtures 97:3, 94:6, 91:9, 88:12 and 85:15. With the n-hexane/ether mixtures 91:9 and 88:12 the 19-methyl selenyl sitosterol was obtained from the column. The fractions in question were evaporated to yield 241 mgs. of pure product. The structural was confirmed by means of NMR-spectrometry (see FIG. 1). From a g.c.-m.s. analysis it appeared that besides the 19-methyl selenyl sitosterol also approximately 7% of the campesterol derivative was present.

EXAMPLE VIII

Preparation of 19-methyl selenyl sitosterol-75 Se (spec. act. 14 m Ci/m Mol)

In an oxygen-free nitrogen atmosphere 1 ml. of tetrahydro furan, freshly distilled from $LiAlH_4$, was added to 80 mgs. of powdered metallic selenium, having an activity of ca. 14 m Ci 75 Se. While the mixture was stirred, at a temperature of −8+ C, methyl lithium in tetrahydro furan was added dropwise until the solution, which was initially dark red, remained colourless for 5 minutes. To the solution of methyl selenide thus prepared at first was added 1.2 mls. of 0.075 M sulphuric acid in dimethoxyethane, freshly distilled from $LiAlH_4$, and then a solution of 457 mgs. of 19-bromo sitosteryl acetate in 4 mls. of dimethoxyethane. After this mixture was kept at ambient temperature for one day, 1 ml. of 0.5 M sodium methoxide in methanol and 2 drops of water were added. This mixture was kept at ambient temperature for 2 hours. After addition of 1 ml. of 2 M $(NH_4)_2 SO_4$ in water the reaction mixture was evaporated to dryness. The residue was mixed with 10 mls. of ethyl ether and transferred (via a paper filter) to a 50 cc. flask. The equipment was rinsed again three times with 10 mls. of ether and the collected etherfractions were evaporated to dryness. The residue thus obtained, containing 9.96 m Ci 75 Se, was taken up into 10 mls. of n-hexane and the mixture was brought on to a column filled with 13 gs. of deactivated $Al_2O_3$. The column was successively eluated with n-hexane and n-hexane/ether mixtures 97:3, 94:6, 91:9, 90:10, 89:11, 88:12, 86:14 and 85:15. With the n-hexane (ether mixtures 94:6 and 91:9, 9.4 m Ci of 19-methyl selenyl sitosterol-75 se was obtained from the column. According to thin-layer chromatography (toluene/ethyl acetate 3:1, silicagel H) this product still contained 19-bromo sitosterol as an impurity. By a repetition of the column chromatography pure 19-methyl selenyl sitosterol-75 Se could be obtained from the product.

EXAMPLE IX

Biological test results

The distribution of 19-methyl selenyl-cholesterol-75 Se (having a specific activity of 10 m Ci per m mol) over a number of internal organs, after intravenous injection, was verified in the following way: From a solution of this 19-methyl selenyl cholesterol-75 Se in ethanol, having a specific activity of 18 μ Ci per ml., each time 0.2 ml. was injected intravenously into the femoral veins of adult male Wistar rats, which had been anaesthetized using a small dosis of ether. After a lapse of 5, 24, 48, 72 and 144 hours from the injection, the test animals were killed and radioactivity was measured of a number of relevant internal organs (corrected for half-value effects) is shown in table A.

TABLE A

| | Percentage of injected dose found in organ after | | | | |
|---|---|---|---|---|---|
| | 5 hours | 24 hours | 48 hours | 72 hours | 144 hours |
| adrenal glands | 0.18 | 0.34 | 0.70 | 0.68 | 0.80 |
| pancreas | 0.22 | 0.45 | 0.45 | 0.51˙ | 0.73 |
| spleen | 4.04 | 3.98 | 1.12 | 0.66 | 0.37 |
| duodenum | 1.16 | 2.04 | 2.21 | 1.60 | 1.30 |
| kidneys | 1.62 | 2.77 | 1.70 | 1.47 | 1.50 |
| liver | 57.19 | 29.57 | 14.78 | 10.84 | 7.46 |

Furthermore, in table B there is shown how the relation between measured radioactivity in the adrenal glands and in the most important ones of the other organs changes in the course of time.

TABLE B

| Relation of the measured radioactivity per g of organ after | | | | | |
|---|---|---|---|---|---|
| | 5 hours | 24 hours | 48 hours | 72 hours | 144 hours |
| adrenal glands /liver | 0.55 | 2.02 | 7.59 | 11.58 | 22.47 |
| adrenal glands /kidneys | 4.46 | 1.22 | 12.71 | 18.47 | 24.29 |
| adrenal glands /spleen | 0.35 | 0.61 | 3.74 | 9.30 | 17.46 |

In a similar way the distribution was determined of 19-methyl selenyl cholesteryl linolate-$^{75}$Se over the same internal organs, after intravenous injections. The results thereof are shown in tables C and D.

TABLE C

| Percentage of the injected dose found in an organ after | | | | | |
|---|---|---|---|---|---|
| | 5 hours | 24 hours | 48 hours | 144 hours | 192 hours | 288 hours |
| adrenal glands | 0.07 | 0.28 | 0.59 | 0.62 | 0.78 | 0.73 |
| pancreas | 0.08 | 0.27 | 0.36 | 0.34 | 0.28 | 0.39 |
| spleen | 4.48 | 2.16 | 1.68 | 1.42 | 0.51 | 0.41 |
| duodenum | 0.82 | 1.59 | 1.77 | 2.53 | 0.70 | 0.83 |
| kidneys | 0.47 | 0.92 | 1.15 | 1.37 | 0.90 | 0.98 |
| liver | 90.62 | 59.95 | 29.78 | 13.90 | 8.02 | 5.95 |

TABLE D

| Relation of the measured radioactivity per g of organ after | | | | | |
|---|---|---|---|---|---|
| | 5 hrs. | 24 hrs. | 48 hrs. | 144 hrs. | 192 hrs. | 288/ hrs. |
| adrenal glands/ liver | 0.094 | 0.68 | 3.12 | 5.32 | 10.76 | 14.33 |
| adrenal glands/ kidneys | 3.39 | 6.82 | 16.33 | 10.04 | 21–20 | 17.64 |
| adrenal glands/ spleen | 0.088 | 0.64 | 2.10 | 2.02 | 7.56 | 9.55 |

In a similar way the distribution was determined of 19-methyl selenyl sitosterol-$^{75}$Se (spec. act. 14 m Ci/m mol) over a number of internal organs, after intravenous injection. The results thereof are shown in tables E and F.

TABLE E

| Percentage of the injected dose found in an organ after | | | | | |
|---|---|---|---|---|---|
| | 4 hours | 24 hours | 48 hours | 120 hours | 240 hours |
| adrenal glands | 0.51 | 0.18 | 0.30 | 0.57 | 0.61 |
| spleen | 12.2 | 1.4 | 1.0 | 0.4 | 0.2 |
| kidneys | 1.7 | 1.4 | 1.5 | 0.9 | 1.0 |
| liver | 120 | 20.8 | 14.2 | 4.7 | 2.5 |

TABLE F

| Relation of the measured radioactivity per g of organ after | | | | | |
|---|---|---|---|---|---|
| | 4 hours | 24 hours | 48 hours | 120 hours | 240 hours |
| adrenal glands/ liver | 0.7 | 2.4 | 6.3 | 30.2 | 47.5 |
| adrenal glands/ kidneys | 11.0 | 8.4 | 12.0 | 30.1 | 29.1 |
| adrenal glands/ spleen | 0.3 | 1.1 | 2.9 | 19.6 | 20.7 |

I claim:
1. Novel selenyl- and telluryl compounds of the formula

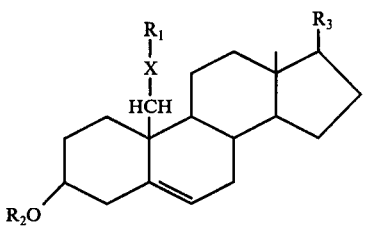

in which X is selected from the group consisting of a selenium and tellurium atom, $R_1$ is a hydrocarbon radical, $R_2$ is selected from the group consisting of a hydrogen atom, an alkanoyl group or an organic group that is easily removed from the oxygen atom, and $R_3$ is a 1,5-dimethyl hexyl optionally containing a member of the group consisting of methyl, and ethyl at the 4-position.

2. A radioactively labelled novel selenyl- and telluryl compound of claim 1, in which X is selected from the group consisting of a selenium isotope and a tellurium isotope.

3. A selenyl- and telluryl compound of claim 1, in which X is selected from the group consisting of selenium and tellurium atoms which may be labelled radioactively, $R_1$ is an alkyl group, $R_2$ is a hydrogen atom and $R_3$ is 1,5-dimethyl hexyl.

4. A selenyl- and telluryl compound of claim 1, in which X is selected from the group consisting of a selenium and tellurium atom which may be labelled radioactively, $R_1$ is an alkyl group, $R_2$ is selected from the group consisting of an alkanoyl-, acetal-, labile ether- and hemiacetal group and $R_3$ is 1,5-dimethyl hexyl.

5. A member of the group consisting of 19-methyl selenyl cholesterol and 19-methyl selenyl cholesterol-$^{75}$Se.

6. A member of the group consisting of 19-methyl selenyl cholesteryl linolate and 19-methyl selenyl cholesteryl linolate and 19-methyl selenyl cholesteryl linolate-$^{75}$Se.

7. 19-methyl telluryl cholesteryl acetate.

8. 19-n-butyl selenyl cholesterol.

9. A member of the group consisting of 19-methyl selenyl sitosterol and 19-methyl selenyl sitosterol-$^{75}$ Se.

10. A process for the preparation of a compound of claim 5 wherein a member of the group consisting of 19-bromocholesteryl acetate and 19-(p-toluene sulfonyl) cholesteryl acetate is reacted with a solution of methyllithium selenide or methyllithium selenide-$^{75}$ Se in tetrahydro furan and, after hydrolysis, the product is isolated.

11. A process for the preparation of a compound of claim 6 wherein a member of the group consisting of 19-bromositosteryl acetate is reacted with a solution of a member of the group consisting of methyllithium selenide and methyllithium selenide-$^{75}$ Se, in the presence of diglyme or triglyme and, after hydrolysis, the product is isolated.

12. A diagnostic composition for diagnostic examination into abnormalities of internal organs, wherein the composition contains, besides a liquid or solid carrier material that can be tolerated by the human body, a radioactively labelled selenyl- or telluryl derivative of a steroid of claim 1.

13. A diagnostic composition according to claim 12, wherein the composition contains 19-methyl selenyl cholesterol-$^{75}$ Se.

14. A diagnostic composition according to claim 12, wherein the composition contains 19-methyl selenyl cholesteryl linolate-$^{75}$ Se.

15. A diagnostic composition according to claim 12, wherein the composition contains 19-methyl selenyl sitosterol-$^{75}$ Se.

16. A method for the diagnostic examination into abnormalities of internal human and animal organs, a radioactive indicator substance being administered and the distribution of this indicator substance over certain internal organs being determined, wherein as an indicator substance there is used a selenyl- or telluryl derivative of a steroid, labelled with a radioactive selenium, or tellurium isotope, respectively, and having the general formula (1) as defined in claim 1.

17. A method according to claim 16, wherein as said indicator substance there is used 19-methyl selenyl cholesterol, that is labelled with $^{75}$ Se.

18. A method according to claim 17, wherein as said indicator substance there is used 19-methyl selenyl-cholesterol-$^{75}$ Se, in an amount corresponding with a radioactivity of 100 to 2000 μ Ci.

19. A method according to claim 16, wherein as said indicator substance there is used 19-methyl selenyl cholesteryl linolate-$^{75}$ Se.

20. A method according to claim 16, wherein as said indicator substance there is used 19-methyl selenyl sitosterol-$^{75}$ Se.

* * * * *

UNITED STATES PATENT OFFICE
CERTIFICATE OF CORRECTION

Patent No. 4,041,145   Dated Aug. 9, 1977

Inventor(s) AUGUSTINUS PETRUS MARIA van der VEEK

It is certified that error appears in the above-identified patent and that said Letters Patent are hereby corrected as shown below:

| Col. | Line | |
|---|---|---|
| 7 | 24 | "example V" should be --Example V-- |
| 7 | 37 | "hereinafter" should be --hereafter-- |
| 8 | 10 | "-8+C" should be --8°C-- |
| 8 | 26 | "etherfraction" should be --ether-fraction-- |
| 8 | 34 | "-75se" should be --75 Se-- |
| 9 | Table D Last Col. | "288/" should be --288-- hrs          hrs |
| 10 Claim 6 | 6 | delete "and 19-methyl selenyl chloesteryl linolate" |

Signed and Sealed this

Twenty-fourth Day of January 1978

[SEAL]

Attest:

RUTH C. MASON
*Attesting Officer*

LUTRELLE F. PARKER
*Acting Commissioner of Patents and Trademarks*